United States Patent [19]

Jahn et al.

[11] Patent Number: 4,740,237
[45] Date of Patent: Apr. 26, 1988

[54] CYCLOHEXANE-1,3-DIONE DERIVATIVES AND THEIR USE FOR CONTROLLING UNDESIRABLE PLANT GROWTH

[75] Inventors: Dieter Jahn, Neckarhausen; Rainer Becker, Bad Durkheim; Norbert Goetz, Worms; Hardo Siegel, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 777,580

[22] Filed: Sep. 19, 1985

Related U.S. Application Data

[63] Continuation of Ser. No. 471,325, Mar. 2, 1983, abandoned.

[30] Foreign Application Priority Data

Mar. 4, 1982 [DE] Fed. Rep. of Germany ....... 3207768
May 25, 1982 [DE] Fed. Rep. of Germany ....... 3219490

[51] Int. Cl.$^4$ .................... A01N 33/08; A01N 37/08; C07C 131/02; C07C 101/02
[52] U.S. Cl. ....................................... 71/121; 71/106; 71/107; 560/37; 560/116; 560/118; 564/256; 564/300; 564/453; 564/455; 564/457

[56] References Cited

U.S. PATENT DOCUMENTS 54-019945 7/1977 JPX .

Primary Examiner—Catherine L. Mills
Attorney, Agent, or Firm—Keil & Weinkauf

[57] ABSTRACT

Cyclohexane-1,3-dione derivatives of the formula

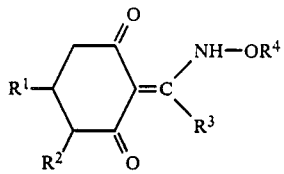

where $R^1$, $R^2$, $R^3$ and $R^4$ have the meanings given in the description, are used for controlling undesirable plant growth.

15 Claims, No Drawings

CYCLOHEXANE-1,3-DIONE DERIVATIVES AND THEIR USE FOR CONTROLLING UNDESIRABLE PLANT GROWTH

This application is a continuation of application Ser. No. 471,325, filed on Mar. 2, 1983, abandoned.

The present invention relates to cyclohexane-1,3-dione derivatives and to herbicides which contain these compounds as active ingredients.

It has been disclosed that cyclohexane-1,3-dione derivatives can be used for selectively controlling undesirable grasses in broadleaf crops (Japanese Preliminary Published Application 79/19945).

We have found that cyclohexane-1,3-dione derivatives of the formula

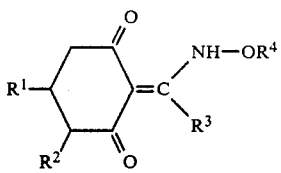

where $R^1$ is cycloalkyl of 3 to 6 carbon atoms which is monosubstituted or polysubstituted by chlorine, bromine, alkyl or alkoxy, each of 1 to 3 carbon atoms, or phenyl, or is a cycloalkyl, bicycloalkyl, tricycloalkyl, cycloalkenyl, bicycloalkenyl or tricycloalkenyl radical of 7 to 12 carbon atoms which is unsubstituted or monosubstituted or polysubstituted by chlorine, bromine, alkyl or alkoxy, each of 1 to 4 carbon atoms, or phenyl, $R^2$ is hydrogen, methoxycarbonyl or ethoxycarbonyl, $R^3$ is alkyl of 1 to 4 carbon atoms and $R^4$ is alkyl of 1 to 3 carbon atoms, alkenyl of 3 or 4 carbon atoms, haloalkenyl of 3 or 4 carbon atoms and 1 to 3 halogen atoms, or propargyl, possess a good herbicidal action against a large number of plant species from the family of the grasses (Gramineae) and are also well tolerated by broadleaf crops and by other crops which do not belong to the Gramineae. Furthermore, certain compounds also possess a selectivity for individual crop plants which also belong to the grasses, eg. rice or wheat.

The compounds of the formula I can occur in a number of tautomeric forms, and all of these are embraced by the claims:

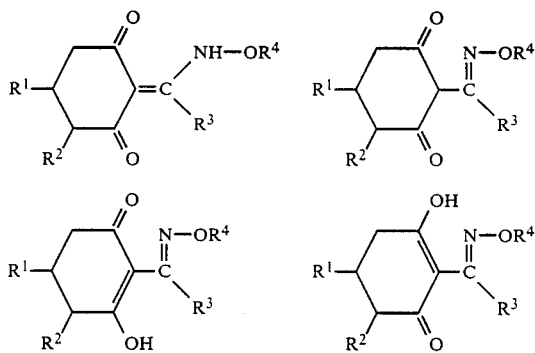

In formula I, $R^1$ is a cycloalkyl, bicycloalkyl or tricycloalkyl radical of 7 to 12 carbon atoms, eg. cycloheptyl, cyclooctyl, cyclononyl, cyclodecyl, cycloundecyl, cyclododecyl, bicycloheptyl, such as bicyclo[2.2.1]hept-2-yl, bicyclooctyl, tricyclooctyl, bicyclononyl, tricyclononyl, bicyclodecyl, tricyclodecyl, bicyclododecyl or tricyclododecyl, or is a cycloalkenyl, bicycloalkenyl or tricycloalkenyl radical of 7 to 12 carbon atoms, such as cycloalkenyl, cycloalkadienyl, cycloalkatrienyl or cycloalkatetraenyl, or the corresponding bicyclic or tricyclic radical containing 1 to 4 double bonds, eg. cycloheptenyl, cyclooctenyl, cyclooctadienyl, cyclononenyl, cyclodecenyl, cyclododecenyl, cyclododecadienyl, such as cyclododeca-1,5-dien-9-yl, cyclododecatetraenyl, such as cyclododeca-1,3,5,7-tetraen-10-yl, bicycloheptenyl, such as bicyclo[2.2.1]hept-2-en-5-yl, bicyclooctenyl, bicyclononenyl, bicyclodecenyl, tricyclodecenyl or bicyclododecadienyl.

These radicals may be monosubstituted or polysubstituted by chlorine, bromine, alkyl of 1 to 4 carbon atoms, eg. methyl, alkoxy of 1 to 4 carbon atoms, eg. methoxy, or phenyl. Examples of radicals $R^1$ of this type are 3,7,7-trimethylbicyclo[4.1.0]hept-4-yl, 2,6,6-trimethylbicyclo[3.1.1]hept-3-yl, 7,7-dichlorobicyclo[4.1.0]hept-3-yl, 4-methyl-7,7-dichlorobicyclo[4.1.0]hept-3-yl, tricyclo[5.2.0$^{2,6}$]dec-8-en-4-yl, tricyclo[5.2.1.0$^{2,6}$]dec-8-en-3-yl and 7,7-dibromobicyclo[4.1.0]hept-3-yl.

$R^1$ can furthermore be cycloalkyl of 3 to 6 carbon atoms which is monosubstituted or polysubstituted by chlorine, bromine, alkyl of 1 to 3 carbon atoms, such as methyl, alkoxy of 1 to 3 carbon atoms, such as methoxy, or phenyl, examples of such radicals $R^1$ being 2,2-dichlorocyclopropyl, 3-phenyl-2,2-dichlorcyclopropyl, 4-methoxycyclohexyl, 2,2,6-trimethylcyclohexyl, 4-chlorocyclohexyl and 2-phenyl-4-methylcyclohexyl.

In formula I, $R^3$ is straight-chain or branched alkyl of 1 to 4 carbon atoms, ie. methyl, ethyl, n-propyl, i-propyl, n-butyl, sec. butyl, i-butyl or tert. butyl.

In formula I, $R^4$ is propargyl, alkyl of 1 to 3 carbon atoms, alkenyl of 3 or 4 carbon atoms or haloalkenyl of 3 or 4 carbon atoms which is substituted by not more than 3 halogen atoms, eg. methyl, ethyl, n-propyl, i-propyl, n-butyl, sec. butyl, i-butyl, tert. butyl, allyl, 1-chloroprop-1-en-3-yl, 2-chloroprop-1-en-3-yl, 1,3-dichloroprop-1-en-3-yl or 1,1,2-trichloroprop-1-en-3-yl.

Examples of suitable salts of the compounds of the formula I are alkali metal salts, in particular potassium or sodium salts, alkaline earth metal salts, in particular calcium, magnesium or barium salts, and manganese, copper, zinc and iron salts.

The compounds of the formula I can be obtained by reacting a compound of the formula

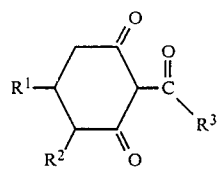

where $R^1$, $R^2$ and $R^3$ have the above meanings, with a hydroxylamine derivative $R^4O-NH_3Y$, where $R^4$ has the above meanings and Y is an anion.

The reaction is advantageously carried out in the heterogeneous phase, in an inert diluent, at from 0° to 80° C. or from 0° C. to the boiling point of the reaction mixture, in the presence of a base. Examples of suitable bases are carbonates, bicarbonates, acetates, alcoholates, hydroxides and oxides of alkali metals and alkaline earth metals, in particular of sodium, potassium, magnesium and calcium. Organic bases, such as pyridine or tertiary amines, can also be used.

The reaction proceeds particularly readily at a pH of from 2 to 8, in particular from 4.5 to 5.5. The pH is advantageously established by the addition of an acetate, for example an alkali metal acetate, in particular sodium acetate or potassium acetate or a mixture of these two salts. The alkali metal acetate is added in an amount of, for example, from 0.5 to 2 moles per mole of the ammonium compound of the formula $R^4O-NH_3Y$.

Examples of suitable solvents are dimethylsulfoxide, alcohols, such as methanol, ethanol and isopropanol, benzene, hydrocarbons and chlorohydrocarbons, such as chloroform, dichloroethane, hexane and cyclohexane, esters, such as ethyl acetate, and ethers such as dioxane and tetrahydrofuran.

The reaction is complete after a few hours, and the product can then be isolated by evaporating down the mixture, adding water, extracting the product with a non-polar solvent, eg. methylene chloride, and distilling off the solvent under reduced pressure.

The compounds of the formula I can also be obtained by reacting a compound of the formula II with a hydroxylamine of the formula $R^4O-NH_2$, where $R^4$ has the above meanings, in an inert diluent at from 0° C. to the boiling point of the reaction mixture, in particular from 15° to 70° C. If appropriate, the hydroxylamine can be employed as an aqueous solution.

Examples of suitable solvents for this reaction are alcohols, such as methanol, ethanol, isopropanol and cyclohexanol, hydrocarbons and chlorohydrocarbons, such as hexane, cyclohexane, methylene chloride, toluene and dichloroethane, esters, such as ethyl acetate, nitriles, such as acetonitrile, and cyclic ethers, such as tetrahydrofuran.

The alkali metal salts of the compounds of the formula I can be obtained by treating these compounds with sodium hydroxide or potassium hydroxide in aqueous solution or in an organic solvent, such as methanol, ethanol or acetone. It is also possible to use a sodium alcoholate or a potassium alcoholate as the base.

The other metal salts, eg. the manganese, copper, zinc, iron, calcium, magnesium and barium salts, can be prepared by reacting a sodium salt with the appropriate metal chloride in aqueous solution.

The compounds of the formula II can be prepared by a conventional method (Tetrahedron Lett., 29 (1975), 2491), from cyclohexane-1,3-diones of the formula III, which can also occur in the tautomeric forms IIIa and IIIb

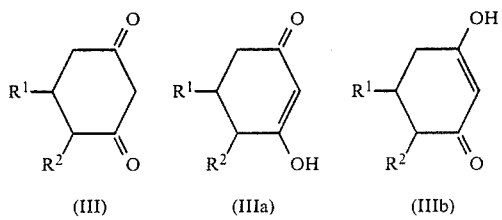

It is also possible to prepare compounds of the formula II via the enol-ester intermediate, which is obtained in the conversion of compounds of the formula II, possibly as an isomer mixture, and undergoes rearrangement in the presence of an imidazole or pyridine derivative (Japanese Preliminary Published Application 79/063052).

The compounds of the formula III are obtained by a conventional process, as represented by the following equation:

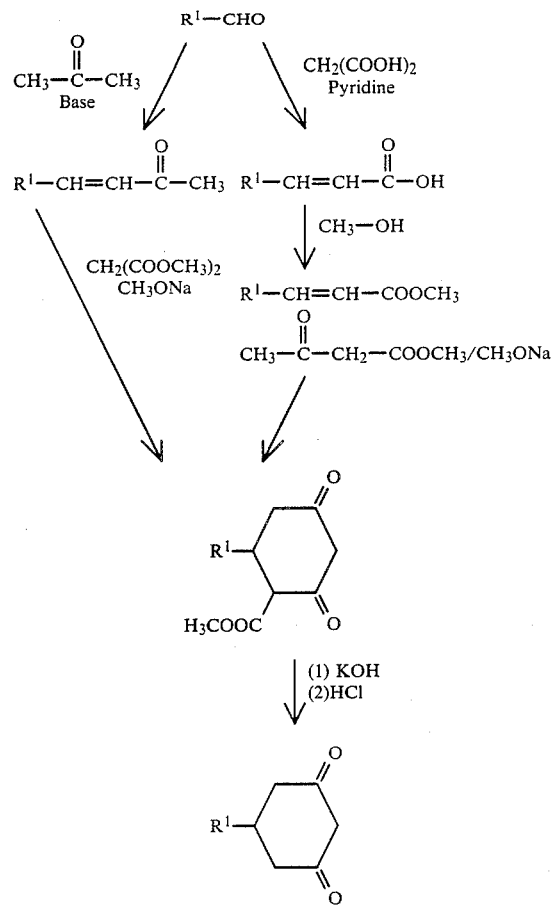

In the Examples which follow, and illustrate the preparation of the cyclohexane-1,3-dione derivatives of the formula I, parts by weight bear the same relation to parts by volume as that of the kilogram to the liter.

EXAMPLE 1

4.9 parts by weight of 2-butyryl-5-cyclooctylcyclohexane-1,3-dione, 1.1 parts by weight of ethoxyamine and 80 parts by volume of ethanol were stirred at room temperature for 12 hours, the solvent was distilled off under reduced pressure, the residue was taken up in 150 parts of dichloromethane, the solution was washed twice with water and dried over sodium sulfate, and the solvent was distilled off under reduced pressure. 2-(1-ethoxyamino-butylidene)-5-cyclooctylcyclohexane-1,3-dione was obtained in 94% yield as an oil (compound no. 1); $n_D^{33}$: 1.5234.

$C_{20}H_{33}NO_3$ (335): calculated: C 71.6, H 9.9, N 4.2, found: C 72.0, H 9.9, N 4.1.

EXAMPLE 2

7.5 parts by weight of 2-propionyl-5-(2,6,6-trimethylbicyclo[3.1.1]-hept-3-yl)-cyclohexane-1,3-dione, 2.9 parts per weight of allyloxyammonium chloride, 2.2 parts by weight of anhydrous sodium acetate and 80 of ethanol were stirred at room temperature for 12 hours, the solvent was distilled off under reduced pressure, the residue was stirred with 120 parts of water and 100 parts of methylene chloride, the organic phase was separated off, the aqueous phase was extracted with 50 parts of methylene chloride, and the combined organic phases were washed with water, dried over sodium sulfate and evaporated down under reduced pressure. 2-(1-allyloxyaminopropylidene)-5-(2,6,6-trimethylbicyclo[3.1.1-]hept-3-yl)cyclohexane-1,3-dione was obtained in 91% yield as an oil (compound no. 2); $n_D^{33}$: 1.5317.

$C_{22}H_{33}NO_3$ (360): calculated: C 73.5, H 9.2, N 3.9, found: C 73.9, H 9.1, N 3.8.

The compounds below were, or may be, obtained in the same manner:

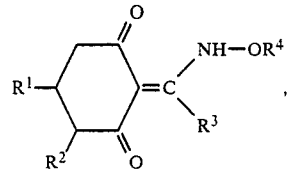
(I)

| No. | $R^1$ | $R^2$ | $R^3$ | | $n_D$ (Temp) |
|---|---|---|---|---|---|
| 3 | cycloheptyl | COOCH$_3$ | n-propyl | ethyl | 1.5172 (23° C.) |
| 4 | cycloheptyl | COOCH$_3$ | n-propyl | allyl | 1.5210 (23° C.) |
| 5 | cycloheptyl | H | n-propyl | ethyl | 1.5240 (20° C.) |
| 6 | cycloheptyl | H | n-propyl | allyl | 1.5291 (23° C.) |
| 7 | cycloheptyl | H | ethyl | ethyl | 1.5292 (20° C.) |
| 8 | cycloheptyl | H | ethyl | allyl | 1.5340 (23° C.) |
| 9 | cycloheptyl | H | ethyl | 3-chloroallyl | |
| 10 | cyclooctyl | H | propyl | allyl | 1.5281 (33° C.) |
| 11 | cyclooctyl | H | propyl | 3-chloroallyl | |
| 12 | cyclooctyl | H | ethyl | ethyl | 1.5322 (16° C.) |
| 13 | cyclooctyl | H | ethyl | allyl | 1.5368 (16° C.) |
| 14 | cycloocten-1-yl-5 | H | n-propyl | ethyl | 1.5345 (23° C.) |
| 15 | cycloocten-1-yl-5 | H | n-propyl | allyl | 1.5390 (23° C.) |
| 16 | cycloocten-1-yl-5 | COOCH$_3$ | n-propyl | ethyl | |
| 17 | cycloocten-1-yl-5 | COOCH$_3$ | n-propyl | allyl | |
| 18 | cyclododecyl | H | n-propyl | ethyl | |
| 19 | cyclododecyl | H | n-propyl | allyl | |
| 20 | cyclododecadien-1,5-yl-9 | H | n-propyl | ethyl | 1.5290 (31° C.) |
| 21 | cyclododecadien-1,5-yl-9 | H | n-propyl | allyl | 1.5332 (31° C.) |
| 22 | 7,7-dichlorobicyclo[4.1.0]heptyl-3 | H | n-propyl | ethyl | 1.5444 (18° C.) |
| 23 | 7,7-dichlorobicyclo[4.1.0]heptyl-3 | H | n-propyl | allyl | 1.5499 (18° C.) |
| 24 | 7,7-dichlorobicyclo[4.1.0]heptyl-3 | H | ethyl | allyl | 1.5535 (18° C.) |
| 25 | 7,7-dichlorobicyclo[4.1.0]heptyl-3 | H | ethyl | athyl | 1.5491 (18° C.) |
| 26 | 3,7 7-trimethylbicyclo[4.1.0]heptyl-4 | H | n-propyl | ethyl | 1.5236 (19° C.) |
| 27 | 3,7 7-trimethylbicyclo[4.1.0]heptyl-4 | H | n-propyl | allyl | 1.5286 (19° C.) |
| 28 | bicyclo[2.2.1]heptyl-2 | H | n-propyl | allyl | |
| 29 | bicyclo[2.2.1]heptyl-2 | H | n-propyl | ethyl | |
| 30 | bicyclo[2.2.1]hepten-2-yl-5 | H | n-propyl | ethyl | 1.5334 (22° C.) |
| 31 | bicyclo[2.2.1]hepten-2-yl-5 | H | n-propyl | allyl | 1.5399 (22° C.) |
| 32 | 2,6,6-trimethylbicyclo[3.1.1]heptyl-3 | H | n-propyl | allyl | 1.5286 (22° C.) |
| 33 | 2,6,6-trimethylbicyclo[3.1.1]heptyl-3 | H | n-propyl | ethyl | 1.5242 (26° C.) |
| 34 | 2,6,6-trimethylbicyclo[3.1.1]heptyl-3 | H | n-propyl | methyl | 1.5298 (26° C.) |
| 35 | 2,6,6-trimethylbicyclo[3.1.1]heptyl-3 | COOCH$_3$ | n-propyl | ethyl | 1.5193 (20° C.) |
| 36 | 2,6,6-trimethylbicyclo[3.1.1]heptyl-3 | COOCH$_3$ | n-propyl | allyl | 1.5245 (20° C.) |
| 37 | 2,6,6-trimethylbicyclo[3.1.1]heptyl-3 | H | ethyl | ethyl | 1.5268 (26° C.) |
| 38 | tricyclo[5.2.1.0$^{2,6}$]decen-8-yl-3 | H | n-propyl | ethyl | |
| 39 | tricyclo[5.2.1.0$^{2,6}$]decen-8-yl-3 | H | n-propyl | allyl | |
| 40 | tricyclo[5.2.1.0$^{2,6}$]decen-8-yl-4 | H | n-propyl | allyl | 1.5478 (22° C.) |
| 41 | tricyclo[5.2.1.0$^{2,6}$]decen-8-yl-4 | H | n-propyl | ethyl | 1.5413 (22° C.) |
| 42 | 2,6,6-trimethylbicyclo[3.1.1]heptyl-3 (sodium salt) | H | n-propyl | ethyl | |
| 43 | 2,6,6-rimethylbicyclo[4.1.1]heptyl-3 (sodium salt) | H | n-propyl | allyl | |
| 44 | 2,2-dichlorocyclopropyl | H | n-propyl | ethyl | 1.5260 (24° C.) |
| 45 | 2,2-dichlorocyclopropyl | H | n-propyl | allyl | 1.5341 (23° C.) |
| 46 | 3-phenyl-2,2-dichlorocyclopropyl | H | ethyl | ethyl | 1.5623 (24° C.) |
| 47 | 3-phenyl-2,2-dichlorocyclopropyl | H | n-propyl | ethyl | 1.5522 (27° C.) |
| 48 | 2,2,6-trimethylcyclohexyl | H | n-propyl | ethyl | 1.5079 (31° C.) |
| 49 | 2,2,6-trimethylcyclohexyl | H | n-propyl | allyl | 1.5219 (31° C.) |
| 50 | 4-methoxy-cyclohexyl | H | n-propyl | ethyl | 1.5138 (22° C.) |
| 51 | 4-methoxy-cyclohexyl | H | n-propyl | allyl | 1.5215 (22° C.) |
| 52 | 2-phenyl-4-methylcyclohexyl | H | n-propyl | allyl | |
| 53 | 2-phenyl-4-methylcyclohexyl | H | n-propyl | ethyl | 1.5512 (25° C.) |
| 54 | 4-methylcyclohexyl | H | n-propyl | ethyl | |
| 55 | 4-methylcyclohexyl | H | n-propyl | allyl | |
| 56 | 4-chlorocyclohexyl | H | n-propyl | allyl | |
| 57 | 4-chlorocyclohexyl | H | n-propyl | ethyl | |
| 58 | 1-phenylcyclohexen-3-yl-6 | H | n-propyl | ethyl | 1.5628 (22° C.) |
| 59 | 1-phenylcyclohexen-3-yl-6 | H | n-propyl | allyl | 1.5653 (22° C.) |
| 60 | cycloheptyl | H | n-propyl | methyl | 1.5296 (26° C.) |
| 61 | cycloheptyl | H | n-propyl | n-propyl | 1.5204 (26° C.) |
| 62 | cycloheptyl | H | n-propyl | propargyl | 1.5335 (26° C.) |
| 63 | bicyclo[2.2.1]hepten-2-yl-5 | H | n-propyl | 3-chloroallyl | 1.5480 (26° C.) |

-continued

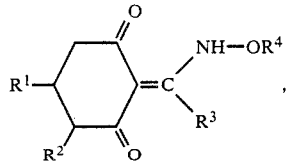

(I)

| No. | $R^1$ | $R^2$ | $R^3$ | $R^4$ | $n_D$ (Temp) |
|---|---|---|---|---|---|
| 64 | bicyclo[2.2.1]hepten-2-yl-5 | H | n-propyl | propargyl | 1.5434 (26° C.) |
| 65 | 2,2-dichlorocyclopropyl | COOCH$_3$ | n-propyl | ethyl | 3.80 (s; COOCH$_3$), 4.15 (q, OCH$_2$) |
| 66 | 3,7,7-trimethylbicyclo[4.1.0]heptyl-4 | COOCH$_3$ | n-propyl | ethyl | 3.79 (s; COOCH$_3$), 4.12 (q, OCH$_2$) |
| 67 | 6,6-dimethylbicyclo[3.1.1]heptan-2-yl-2 | H | n-propyl | ethyl | 4.10 (q; OCH$_2$), 5.30 (s; =CH) |
| 68 | 6,6-dimethylbicyclo[3.1.1]heptan-2-yl-2 | H | n-propyl | allyl | 2.90 (t; $-\overset{\underset{\|}{N-}}{C}-CH_2$), 4.55 (d; OCH$_2$) |
| 69 | 6,6-dimethylbicyclo[3.1.1]heptan-2-yl-2 | H | n-propyl | 3-chloroallyl | 1.535 (24° C.) |
| 70 | 4-tert.-butoxy-cyclohexyl | H | n-propyl | ethyl | |
| 71 | cyclododecadien-1,5-yl-9 | H | n-propyl | 3-chloroallyl | |
| 72 | cyclododecadien-1,5-yl-9 | H | n-propyl | propargyl | |
| 73 | cyclododecadien-1,5-yl-9 | H | n-propyl | n-propyl | |
| 74 | cyclododecadien-1,5-yl-9 | H | Ethyl | n-propyl | |
| 75 | cyclododecadien-1,5-yl-9 | H | ethyl | allyl | |
| 76 | cyclododecadien-1,5-yl-9 | H | ethyl | 3-chloroallyl | |
| 77 | cyclododecadien-1,5-yl-9 | H | ethyl | ethyl | |
| 78 | cyclododecadien-1,5-yl-9 | H | ethyl | propargyl | |
| 79 | cyclododecadien-1,5-yl-9 | H | methyl | propargyl | |
| 80 | cyclododecadien-1,5-yl-9 | H | methyl | n-propyl | |
| 81 | cyclododecadien-1,5-yl-9 | H | methyl | ethyl | |
| 82 | cyclododecadien-1,5-yl-9 | H | methyl | allyl | |
| 83 | cyclododecyl | H | n-propyl | 3-chloroallyl | |
| 84 | cyclododecyl | H | n-propyl | propargyl | |
| 85 | cyclododecyl | H | ethyl | ethyl | |
| 86 | cyclododecyl | H | ethyl | allyl | |
| 87 | cyclododecyl | H | ethyl | 3-chloroallyl | |
| 88 | cyclododecyl | H | ethyl | propargyl | |
| 89 | cyclododecatetraen-1,3,5,7-yl-10 | H | n-propyl | ethyl | |
| 90 | cyclododecatetraen-1,3,5,7-yl-10 | H | n-propyl | allyl | |
| 91 | cyclooctatrien-1,3,5-yl-7 | H | n-propyl | allyl | |
| 92 | cyclooctatrien-1,3,5-yl-7 | H | n-propyl | ethyl | |
| 93 | cyclooctadien-1,3-yl-6 | H | n-propyl | ethyl | |
| 94 | cyclooctadien-1,3-yl-6 | H | n-propyl | allyl | |
| 95 | cyclododecadien-1,5-yl-9(sodium salt) | H | n-propyl | ethyl | |
| 96 | cyclododecadien-1,5-yl-9(sodium salt) | H | n-propyl | allyl | |
| 97 | cycloheptyl | H | n-propyl | methyl | |
| 98 | cycloheptyl | H | n-propyl | n-propyl | |
| 99 | cycloheptyl | H | n-propyl | propargyl | |
| 100 | 1,4(3)-dimethylcyclohexen-3-yl | H | n-propyl | ethyl | |

The cyclohexane-1,3-dione derivatives of the formula I may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of compound no. 1 is mixed with 10 parts by weight of N-methyl-alpha-pyrrolidone. A mixture is obtained which is suitable for application in the form of very fine drops.

II. 20 parts by weight of compound no. 2 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound no. 10 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound no. 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into 100,000 parts by weight of water and uniformly distributing it therein, an aqueous dispersion is obtained containing 0.02% by weight of the active ingredient.

V. 80 parts by weight of compound no. 2 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound no. 1 is intimately mixed with 95 parts by weight of particulate kaolin. A dust is obtained containing 5% by weight of the active ingredient.

VII. 30 parts by weight of compound no. 11 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 5 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or post-emergence. Preferably, the active ingredients, or agents containing them, are applied after emergence of the unwanted plants. If certain crop plants tolerate the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved and the growth stage of the plants, and varies from 0.025 to 5 kg/ha and more.

The herbicidal action of cyclohexane-1,3-dione derivatives of the formula I on the growth of plants from the Gramineae family and broadleaf crop plants is demonstrated in greenhouse experiments.

The vessels employed were plastic flowerpots having a volume of 300 cm$^3$, and which were filled with a sandy loam containing about 1.5% humus. The seeds of the test plants were sown shallow, and separately, according to species. For the preemergence treatment, the active ingredients were applied to the surface of the soil immediately after the seeds had been sown. The compounds were emulsified or suspended in water as vehicle, and sprayed through finely distributing nozzles. The application rate was 3.0 kg of active ingredient per hectare. After the agents had been applied, the vessels were lightly sprinkler-irrigated to induce germination and growth and to activate the chemical agents. Transparent plastic covers were then placed on the vessels until the plants had taken root. The cover ensured uniform germination of the plants, insofar as this was not impaired by the chemicals.

For the postemergence treatment, the plants were first grown in the vessels to a height of from 3 to 15 cm, depending on growth form, before being treated. The rice, soybean and bushbean plants used in this treatment were grown in a peat-enriched substrate. No impairment of the results need be feared because the active ingredients were applied to the foliage. For this treatment, either plants which had been sown directly in the pots and grown there were selected, or plants which had been grown separately as seedlings and transplanted to the experiment vessels a few days before treatment. No covers were placed on the pots in this treatment method. The application rates for postemergence treatment varied from ingredient to ingredient, and were 0.125, 0.25, 0.5 and 1.0 kg of active ingredient per hectare.

The pots were set up in the greenhouse—species from warmer areas at from 20° to 35° C., and species from moderate climates at 10° to 25° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Avena fatua, Avena sativa, Beta vulgaris, Bromus tectorum, Digitaria sanguinalis, Echinochloa crus-galli, Glycine max., Gossypium hirsutum, Lolium multiflorum, Oryza sativa, Phaseolus vulg., Setaria italica, Sorghum halepense, Triticum aestivum,* and *Zea mays.*

On investigations into the herbicidal action on preemergence application, for example compounds nos. 1, 2, 5, 6, 10, 13, 20, 22, 23, 24, 25, 26, 27, 32, 34, 35 and 37, had, at a rate of 3.0 kg/ha, a considerable herbicidal action on grassy plants.

On investigations into selective herbicidal properties on postemergence application, for instance compounds nos. 20, 32 and 33 combated grass species very well at 0.125 and 1.0 kg/ha. Compound no. 22, at 0.25 kg/ha, also had a good herbicidal action on unwanted grassy crop plants, and was tolerated by wheat and rice. Compounds nos. 32 and 33, at 1.0 kg/ha, were well tolerated by broadleaf crops, and caused considerable damage to grassy species.

In view of their tolerance, and the many methods possible of applying them, the compounds according to the invention may be used in a further, large number of crops for removing unwanted wild grasses or grassy crop plants growing where they are not desired.

The following crop plants may be mentioned by way of example:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | turnips |
| *Brassica napus* var. *rapa* | |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | mandarins |
| *Citrus sinensis* | orange trees |

-continued

| Botanical name | Common name |
| --- | --- |
| *Coffea arabica* (*Coffea canephora, Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum Gossypium herbaceum Gossypium vitifolium*) | cotton |
| *Helianthus annuus* | sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor* (*s. vulgare*) | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis* (*V. unguiculata*) | cow peas |
| *Vitis vinifera* | grapes |
| *Zea mays* | Indian corn, sweet corn, maize |

To increase the spectrum of action and to achieve synergistic effects, the cyclohexane-1,3-dione derivatives of the formula I may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocyrboxylic acids, triazines, amides, ureas, diphenyl ethers, triazinones, uracils, benzofuran derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

We claim:

1. A cyclohexane-1,3-dione derivative of the formula

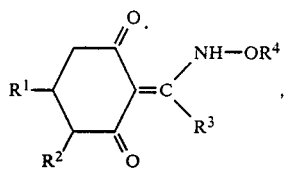

where $R^1$ is a cyclohexyl radical which is mono-substituted or polysubstituted by alkyl or alkoxy, each of 1 to 4 carbon atoms, or phenyl or is a cycloalkyl, bicycloalkyl, tricycloalkyl, cycloalkenyl, bicycloalkenyl or tricycloalkenyl radical of 7 to 12 carbon atoms which is unsubstituted or mono-substituted or polysubstituted by chlorine, bromine, alkyl or alkoxy, each of 1 to 4 carbon atoms, or by phenyl, $R^2$ is hydrogen, methoxycarbonyl or ethoxycarbonyl, $R^3$ is alkyl of 1 to 4 carbon atoms and $R^4$ is alkyl of 1 to 3 carbon atoms, alkenyl of 3 or 4 carbon atoms, haloalkenyl of 3 or 4 carbon atoms and 1 to 3 halogen atoms, or propargyl, or a salt thereof.

2. 2-(1-Ethoxyaminobutylidene)-5-(cyclododeca-1,5-dien-9-yl)-cyclohexane-1,3-dione.

3. 2-(1-Allyloxyaminobutylidene)-5-(cyclododeca-1,5-dien-9-yl)-cyclohexane-1,3-dione.

4. A herbicide containing inert additives and a herbicidally effective amount of a cyclohexane-1,3-dione derivative as claimed in claim 1.

5. A herbicide as claimed in claim 4, containing 2-(1-ethoxyaminobutylidene)-5-(cyclododeca-1,5-dien-9-yl)-cyclohexane-1,3-dione as cyclohexane-1,3-dione derivative of the formula I.

6. A herbicide as claimed in claim 4, containing 2-(1-allyloxyaminobutylidene)-5-(cyclododeca-1,5-dien-9-yl)-cyclohexane-1,3-dione as cyclohexane-1,3-dione derivative of the formula I.

7. A herbicide as claimed in claim 4, containing from 0.1 to 95 wt% of a cyclohexane-1,3-dione derivative of the formula I as claimed in claim 1.

8. A process for combating the growth of unwanted plants, wherein the plants and/or the areas to be kept free from unwanted plant growth are treated with a herbicidally effective amount of a cyclohexane-1,3-dione derivative of the formula I as claimed in claim 1.

9. A cyclohexane-1,3-dione of the formula I as defined in claim 1, wherein $R^1$ is cycloalkyl or bicycloalkyl of 7 to 12 carbon atoms.

10. A cyclohexane-1,3-dione of the formula I as defined in claim 1, wherein $R^2$ is hydrogen, $R^3$ is propyl and $R^4$ is ethyl or allyl.

11. The cyclohexane-1,3 dione derivative of the formula I as defined in claim 1 which is 2-(1-allyloxyaminobutylidene)-5-(2,6,6-trimethylbicyclo(3.1.1)hept-3-yl)-cyclohexane-1,3-dione.

12. The cyclohexane-1,3 dione derivative of the formula I as defined in claim 1 which is 2-(1-ethoxyaminobutylidene)-5-(-4-methylcyclohexyl)-cyclohexane-1,3-dione.

13. The cyclohexane-1,3-dione derivative of the formula I as defined in claim 1 which is (2-(1-allyloxyaminobutylidene)-5-(4-methylcyclohexyl)-cyclohexane-1,3-dione.

14. The compound 2-(1-ethoxyaminopropylidene)5-(4-tertiary-butoxy-cyclohexyl)-cyclohexane-1,3-dione.

15. A process for combating the growth of unwanted plants, wherein the plants and/or the areas to be kept free from unwanted plant growth are treated with a herbicidally effective amount of the compound as set forth in claim 14.

* * * * *